(12) United States Patent
Seo et al.

(10) Patent No.: US 9,446,052 B2
(45) Date of Patent: Sep. 20, 2016

(54) COMPOSITION FOR PREVENTION OF NAUSEA OR VOMITING

(75) Inventors: Min Hyo Seo, Daejeon (KR); Sa Won Lee, Daejeon (KR); Do Hoon Kim, Seoul (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 0 days.

(21) Appl. No.: 13/976,199

(22) PCT Filed: Dec. 21, 2011

(86) PCT No.: PCT/KR2011/009908
§ 371 (c)(1),
(2), (4) Date: Jun. 26, 2013

(87) PCT Pub. No.: WO2012/091357
PCT Pub. Date: Jul. 5, 2012

(65) Prior Publication Data
US 2013/0267487 A1 Oct. 10, 2013

(30) Foreign Application Priority Data
Dec. 27, 2010 (KR) .................. 10-2010-0135761

(51) Int. Cl.
*A61K 31/573* (2006.01)
*A61K 31/4178* (2006.01)
*A61K 9/00* (2006.01)
*A61K 45/06* (2006.01)
*A61K 47/12* (2006.01)
*A61K 31/4184* (2006.01)

(52) U.S. Cl.
CPC ........... *A61K 31/573* (2013.01); *A61K 9/0019* (2013.01); *A61K 31/4178* (2013.01); *A61K 31/4184* (2013.01); *A61K 45/06* (2013.01); *A61K 47/12* (2013.01)

(58) Field of Classification Search
USPC ...................................................... 514/171
See application file for complete search history.

(56) References Cited

U.S. PATENT DOCUMENTS

| | | | | |
|---|---|---|---|---|
| 5,929,059 A * | 7/1999 | Sanger et al. | ................ | 514/171 |
| 2002/0055495 A1 | 5/2002 | Jannetta | | |
| 2006/0074101 A1 | 4/2006 | Baroni et al. | | |
| 2006/0167073 A1* | 7/2006 | Calderari et al. | ............. | 514/397 |

FOREIGN PATENT DOCUMENTS

| | | |
|---|---|---|
| EP | 1 970 049 A1 | 9/2008 |
| JP | 6-507152 A | 8/1994 |
| JP | 2006-516583 A | 7/2006 |
| WO | WO 92/12716 | 8/1992 |
| WO | WO 2004/067005 A1 | 8/2004 |
| WO | WO 2005/056008 A1 | 6/2005 |
| WO | WO 2006/124807 A1 | 11/2006 |
| WO | WO 2007/090091 A2 | 8/2007 |
| WO | WO 2007/106381 A2 | 9/2007 |
| WO | WO 2010/119300 A2 | 10/2010 |

OTHER PUBLICATIONS

Morgan Griffin Control Chemotherapy Nausea and Vomiting (2009).*
Merck Sharp & Dohme-Chibret Laboratories (Nov. 29, 2006).*
The Italian Group for Antimetic Research (The New England Journal of Medicine 342(21); 1554-1559 (2000.*
Fernando et al. (BJA, 2009; 285-286).*
Wang et al Can J Anesth 2001 / 48: 2 / pp. 185-190.*
International Search Report from International Application No. PCT/KR2011/009908 mailed Jun. 21, 2012.
Perez, "Use of Dexamethasone with 5-HT$_3$-Receptor Antagonists for Chemotherapy-Induced Nausea and Vomiting," *Cancer Journal from Scientific American*, 4(2):72-77 (1998).
Jordan et al., "Comparative activity of antiemetic drugs," *Critical Reviews in Oncology/Hematology*, 61:162-75 (2007).
Oettle et al., "Treatment of chemotheraphy-induced nausea and vomiting," *J Cancer Res Clin Oncol*, 127:340-45 (2001).
Office Action for corresponding Japanese Patent Application No. 2013-547312 (mailed Jul. 18, 2014).
Extended European Search Report for corresponding European Patent Application No. 11 854 386.7 (mailed Aug. 27, 2014).
Evrard et al., "Stability of ondansetron hydrochloride and dexamethasone sodium phosphate in 0.9% sodium chloride injection and in 5% dextrose injection", *Am J Health-Syst Pharm*, 54: 1065-68 (1997).
Hagan et al., "Stability of ondansetron hydrochloride and dexamethasone sodium phosphate in infusion bags and syringes for 32 days", *Am J Health-Syst Pharm*, 53: 1431-35 (1996).
Perez et al., "Use of Dexamethasone with 5-HT3- Receptor Antagonists for Chemotherapy-Induced Nausea and Vomiting", *The Cancer Journal from Scientific American*, 4(1):72-77 (1998).
Jordan et al., "Comparative activity of antiemetic drugs", *Critical Reviews in Oncology/Hematology*, 61: 162-75 (2007).
Walker et al., "Stability and Compatibility of Granisetron Alone and in Combination with Dexamethasone in 0.9% Sodium Chloride and 5% Dextrose in Water Solutions", *Can J Hosp Pharm*, 55:27-38 (2002).
Office Action from corresponding Chinese Application No. 201180068557.3 (mailed Jun. 24, 2014).
Mayron et al., "Stability and compatibility of granisetron hydrochloride in i.v. solutions and oral liquids and during simulated Y-site injection with selected drugs", *Am J Health-Syst Pharm*, 53: 294-304 (1996).

* cited by examiner

*Primary Examiner* — Shirley V Gembeh
(74) *Attorney, Agent, or Firm* — Merchant & Gould P.C.

(57) ABSTRACT

Provided is a composition for preventing nausea or vomiting, including a 5-HT$_3$ receptor antagonist and a corticosteroid, and having a pH adjusted to 3.0-6.0. Provided also is a method for preparing a composition for preventing nausea or vomiting, including: mixing a 5-HT$_3$ receptor antagonist with a corticosteroid; and adjusting pH of the mixture obtained from the preceding operation to 3.0-6.0.

9 Claims, No Drawings

COMPOSITION FOR PREVENTION OF NAUSEA OR VOMITING

This application is a U.S. National Stage Application under 35 U.S.C. §371 of International Patent Application No. PCT/KR2011/009908, filed 21 Dec. 2011, which claims the benefit of priority to Korean Patent Application No. 10-2010-0135761, filed 27 Dec. 2010, the disclosures of all of which are hereby incorporated by reference in their entireties. The International Application was published in English on 5Jul. 2012 as WO 2012/091357.

TECHNICAL FIELD

This disclosure relates to a composition for preventing nausea or vomiting and a method for preparing the same.

BACKGROUND ART

Nausea, also referred to as the condition of feeling sick, means the feeling that one is going to vomit. Vomitting is the condition of discharging contents in a digestive tract out through one's mouth. In general, nausea and vomiting conditions result from overeating, heavy drinking, diseases in a digestive system, various infectious diseases, side effects of drugs or chemicals, or the like. Particularly, the nausea and vomiting condition caused by anti-cancer chemotherapy, radiotherapy or the like is one of the main side effects that make it difficult to perform effective treatment of patients suffering from cancer. In addition, the nausea and vomiting condition generated when patients are recovered from anesthesia after surgery is one of the main causes of degrading the quality of patient's life. Therefore, there is a need for developing an effective method or agent for preventing, inhibiting or treating nausea and vomiting.

DISCLOSURE OF INVENTION

Technical Problem

This disclosure is directed to providing a composition for preventing nausea or vomiting. This disclosure is also directed to providing a method for preparing a composition for preventing nausea or vomiting.

Solution to Problem

In one general aspect, there is provided a composition for preventing nausea or vomiting, including a 5-$HT_3$ receptor antagonist and a corticosteroid, and having a pH adjusted to 3.0-6.0.

In another general aspect, there is provided a method for preparing a composition for preventing nausea or vomiting, including: mixing a 5-$HT_3$ receptor antagonist with a corticosteroid; and adjusting pH of the mixture obtained from the preceding operation to 3.0-6.0.

In still another general aspect, there is provided a composition for preventing nausea or vomiting, obtained by the above method.

Advantageous Effects of Invention

The composition according to one embodiment is effective for preventing, inhibiting or treating nausea or vomiting. Even though the composition includes no solubilizer or the like, it shows high stability without any precipitation and decomposition of its active ingredients while it is stored in an aqueous solution state at room temperature. In addition, the composition may be administered directly to a subject without dilution. Particularly, when the composition is used for injection, it is possible to administer both a 5-$HT_3$ receptor antagonist and a corticosteroid in a unit dose. As a result, it is possible to solve the patient's inconvenience caused by frequent injection, thereby improving the patient's compliance and saving the cost required for preparing drugs.

Mode for the Invention

Hereinafter, the embodiments of the present disclosure will be described in detail.

Nausea and vomiting conditions occurring after anti-cancer chemotherapy or radiotherapy may be classified, depending on the time to occurrence after treatment, into acute types (occurrence within 24 hours) and delayed types (occurrence after 24 hours or more). 5-$HT_3$ receptor antagonists that have been developed and used widely as agents for preventing or inhibiting nausea and vomiting are very effective for preventing or controlling acute types of nausea and vomiting. However, it is known that such 5-$HT_3$ receptor antagonists are not significantly effective for preventing or inhibiting delayed types of nausea and vomiting. Meanwhile, it is known that corticosteroids, such as dexamethasone, are effective for preventing or inhibiting delayed types of nausea and vomiting.

For this reason, the following drug therapy has recommended as an effective way for preventing vomiting and nausea occurring when patients are recovered from anesthesia after anti-cancer chemotherapy, radiotherapy or surgery. First, a 5-$HT_3$ receptor antagonists and a corticosteroid are administered to a patient subjected to administration of a drug having high possibility of causing acute nausea and vomiting. Then, a corticosteroid, such as dexamethasone, is administered for 2-4 days to prevent delayed nausea and vomiting.

A commercially available ondansetron injection formulation (e.g. Zofran®) generally includes ondansetron in its hydrochloride form solubilized in aqueous solution with pH 3-4. A commercially available dexamethasone injection formulation is generally provided as aqueous solution of a dexamethasone phosphate derivative and is a composition having a pH of 7.5-9.0.

With regard to a method for preventing or treating nausea and vomiting by administering ondansetron as a 5-$HT_3$ receptor antagonist in combination with dexamethasone as a corticosteroid, oral compositions, such as tablet and capsule compositions, have been known as compositions including ondansetron in combination with dexamethasone. However, since ondansetron and dexamethasone are not soluble in water at pH 6-7.5, simple combination thereof using no suitable solubilizer causes crystal precipitation. Therefore, it is substantially impossible to prepare an injection composition including both ondansetron and dexamethasone in solubilized forms.

When providing a stable injection composition including a 5-$HT_3$ receptor antagonist in combination with a corticosteroid, it is possible to improve an effect of preventing or treating nausea or vomiting. It is also possible to solve the patient's inconvenience caused by frequent injection, and thus to increase the patient's compliance. Further, it is possible to save the cost required for preparing drugs.

Under these circumstances, the present inventors have conducted many studies to provide a mixed aqueous composition that allows coadministration of a 5-HT$_3$ receptor antagonist, such as ondansetron, with a corticosteroid, such as dexamethasone.

In one aspect, there is provided a composition for preventing nausea and vomiting, including a 5-HT$_3$ receptor antagonist and a corticosteroid and having a pH adjusted to 3.0-6.0. The composition for preventing nausea and vomiting shows high stability while causing no precipitation and decomposition of its active ingredients, even when it is stored in an aqueous solution state at room temperature. In addition, the composition may be administered directly to a subject without dilution.

In another aspect, there is provided a method for preparing composition for preventing nausea or vomiting, including: mixing a 5-HT$_3$ receptor antagonist with a corticosteroid; and adjusting pH of the mixture obtained from the preceding operation to 3.0-6.0.

According to one embodiment, the 5-HT$_3$ receptor antagonist includes any material that shows antagonism against a 5-HT$_3$ receptor. According to another embodiment, the 5-HT$_3$ receptor antagonist includes at least one selected from the group consisting of ondansetron, ramosetron, granisetron, tropisetron, dolasetron, palonosetron, alosetron, lurosetron, derivatives thereof and pharmaceutically acceptable salts thereof.

The composition according to one embodiment may include the 5-HT$_3$ receptor antagonist at a concentration of 0.01 mg/mL to 10 mg/mL. According to another embodiment, the composition may include the 5-HT$_3$ receptor antagonist at a concentration of 0.05 mg/mL to 0.3 mg/mL or 1 mg/mL to 4 mg/mL. The concentration of the 5-HT$_3$ receptor antagonist may be varied with the particular type of active ingredient or formulation.

As used herein, the term 'corticosteroid' generally includes any chemicals called steroids. According to one embodiment, the corticosteroid includes any one having an effect of inhibiting nausea or vomiting. According to another embodiment, the corticosteroid includes at least one selected from the group consisting of dexamethasone, derivatives thereof and pharmaceutically acceptable salts thereof. According to still another embodiment, the group consisting of dexamethasone, derivatives thereof and pharmaceutically acceptable salts thereof includes dexamethasone acetate or dexamethasone disodium phosphate.

The composition according to one embodiment may include the corticosteroid at a concentration of 0.01 mg/mL to 10 mg/mL. According to another embodiment, the composition may include the corticosteroid at a concentration of 0.05 mg/mL to 0.3 mg/mL or 1 mg/mL to 4 mg/mL. The concentration of the corticosteroid may be varied with the particular type of active ingredient or formulation.

As used herein, the 5-HT$_3$ receptor antagonist or corticosteroid, or derivatives thereof cover their free forms (free acid or free base forms), prodrugs, polymorphs, hydrates, solvates, tautomers or stereoisomers. In addition, the pharmaceutically acceptable salts include, but are not limited to, those of at least one acid selected from the group consisting of hydrochloric acid, hydrobromic acid, sulfuric acid, sulfurous acid, phosphoric acid, citric acid, acetic acid, maleic acid, fumaric acid, glycolic acid, succinic acid, tartaric acid, glutamic acid, methanesulfonic acid and aspartic acid.

According to one embodiment, the composition may be adjusted to a pH of 3.0-4.5. According to another embodiment, the composition may be adjusted to a pH of 3.5-4.5. When pH is adjusted to the above-defined range, it is possible to obtain a stable composition causing no precipitation and decomposition of the active ingredients.

The composition according to one embodiment may further include a pH modifier or a buffering agent. According to another embodiment, a pH modifier or a buffering agent may be used for the purpose of pH adjustment, wherein the pH modifier or a buffering agent includes those currently used in the related art. Non-limiting examples of the pH modifier that may be used herein include at least one selected from the group consisting of organic acids, such as acetic acid, citric acid, lactic acid, maleic acid, adipic acid, tartaric acid and benzoic acid, hydrochloric acid, phosphoric acid, carbonic acid and cyanic acid. Non-limiting examples of the buffering agent that may be used herein include at least one selected from the group consisting of organic acid buffers, such as acetic acid, citric acid, lactic acid, maleic acid, adipic acid, tartaric acid and benzoic acid, phosphate buffers and carbonate buffers.

According to still another embodiment, it is possible to adjust pH by using an adequate amount of pH modifier or buffering agent as a function of mixing ratio of the 5-HT$_3$ receptor antagonist with the corticosteroid.

In still another aspect, there is provided a pharmaceutical composition for preventing nausea and vomiting, including a 5-HT$_3$ receptor antagonist and a corticosteroid and having a pH adjusted to 3.0-6.0. The pharmaceutical composition may be applied to animals including humans.

When applying the composition disclosed herein to pharmaceuticals, currently used inorganic or organic carriers are added to the composition containing active ingredients, so that the composition may be formulated into solid, semi-solid or liquid formulations for oral or parenteral administration. Particularly, the composition may be provided as a liquid composition. When the composition is provides as a formulation in the form of aqueous solution, it shows high stability without crystal precipitation even at room temperature, and thus has high applicability. The composition disclosed herein may be formulated with ease by a method generally known to those skilled in the art. If desired, a surfactant, excipient, coloring agent, flavor, stabilizing agent, preservative, antiseptic, hydrating agent, emulsifier, suspending agent, osmotic pressure-adjusting salt and/or other buffering agents or other conventional adjuvants may be used.

For oral administration, tablets, pills, granules, soft and hard capsules, dusts, fine particles, powder, liquid, emulsion, syrup, pellets, etc. may be used, and liquid formulations may be frequently used. Such formulations may further include diluents (e.g. lactose, dextrose, sucrose, mannitol, sorbitol, cellulose or glycine) or lubricants (e.g. silica, talc, stearic acid and magnesium or calcium salts thereof or polyethylene glycol), in addition to the active ingredients. Tablets may include a binder such as magnesium aluminum silicate, starch paste, gelatin, tragacanth, methyl cellulose, sodium carboxymethyl cellulose or polyvinyl pyrrolidone. If necessary, tablets may further include other pharmaceutical additives, for example, a disintegrating agent, such as starch, agar, alginic acid or a sodium salt thereof, adsorbing agent, coloring agent, flavor or sweetener. Such tablets may be obtained by conventional mixing, granulation or coating processes.

Meanwhile, formulations for parenteral administration include injection formulations, drops, suppositories, patches, films, strips or spray formulations, but are not limited thereto. Particularly, the composition disclosed herein may be provided as injection formulations or drops.

The pharmaceutical composition disclosed herein may be administered via oral, parenteral, rectal, local, transdermal, intravenous, intramuscular, intraperitoneal, subcutaneous routes, or the like.

In addition, the dose of active ingredients may be varied with the age, sex and body weight of a subject to be treated, particular disease or pathological condition to be treated, severity of disease or pathological condition, administration route and the judgment of a prescriber. Determination of the effective dose may be made by those skilled in the art based on the above-mentioned factors. In general, the effective dose may be between 0.001 mg/kg/day and 2000 mg/kg/day, particularly between 0.1 mg/kg/day and 20 mg/kg/day, and more particularly between 0.1 mg/kg/day and 1.0 mg/kg/day, or between 5.0 mg/kg/day and 20 mg/kg/day.

In yet another aspect, there is provided a composition for preventing, inhibiting or treating nausea or vomiting, obtained by the above-described method for preparing a composition for preventing, inhibiting or treating nausea or vomiting. The composition obtained by the method shows high stability without any precipitation and decomposition of its active ingredients while it is stored in an aqueous solution state at room temperature. In addition, the composition may be administered directly to a subject without dilution.

The examples and comparative examples will now be described. The following examples and comparative examples are for illustrative purposes only and not intended to limit the scope of this disclosure.

COMPARATIVE EXAMPLE 1

Preparation of Mixture of Ondansetron Hydrochloride with Dexamethasone Disodium Phosphate Comparative Example 1 is provided by simple mixing of 5 mL of the conventional injection composition of ondansetron hydrochloride with 5 mL of the conventional aqueous composition of dexamethasone disodium phosphate. Each composition has an effect of preventing nausea or vomiting.

1) Conventional Injection Composition of Ondansetron Hydrochloride
  Ondansetron hydrochloride: 2 mg/mL
  Sodium chloride: 9 mg/mL
  Citric acid monohydrate: 0.5 mg/mL
  Sodium citrate dehydrate: 0.25 mg/mL
  pH of aqueous solution: 3.5

2) Conventional Injection Composition of Dexamethasone Disodium Phosphate
  dexamethasone disodium phosphate: 2 mg/mL
  pH of aqueous composition: 8.5

White crystal precipitation occurs right after the mixing, and the mixed aqueous solution has a pH of 6.4. It can be seen from the above result that simple mixing of the two injection compositions cannot provide a stable composition.

EXAMPLES 1-4 AND COMPARATIVE EXAMPLE 2

Preparation of Mixture of Ondansetron Hydrochloride with Dexamethasone Disodium Phosphate Examples 1-4 and Comparative Example 2 are provided by using the compositions and amounts as shown in the following Table 1. More particularly, ondansetron hydrochloride dehydrate is added to and dissolved in 45 mL of 0.9% saline for injection. Then, dexamethasone disodium phosphate is added thereto and the mixture is agitated. When white crystal precipitation occurs, citric acid monohydrate is added to form a clear solution. The aqueous solution is adjusted to a pH range of 3.0-4.5 by adding sodium citrate. Then, distilled water for injection is added to the aqueous solution, until the total volume of the aqueous solution becomes 25 or 50 mL. The mixed solution is sterilized with a sterilization filter having a pore size of 0.22 μm, and an aliquot of 5 mL of each sample is put into a 10 mL injection vial, followed by sealing. In this manner, Examples 1-4 are provided. Comparative Example 2 is provided by adding 0.1N HCl instead of citric acid to adjust the pH to 2.5. After the sample preparation, each sample is observed for crystal precipitation.

TABLE 1

| Example | Ondansetron Hydrochloride (mg) | Dexamethasone disodium phosphate (mg) | Volume of Aqueous Solution (mL) | pH | Precipitation |
|---|---|---|---|---|---|
| Example 1 | 100 | 100 | 50 | 4.0 | Clear |
| Example 2 | 100 | 100 | 25 | 4.0 | Clear |
| Example 3 | 50 | 100 | 50 | 4.0 | Clear |
| Example 4 | 100 | 50 | 50 | 4.0 | Clear |
| Comparative Example 2 | 100 | 100 | 50 | 2.5 | Precipitation |

As can be seen from the above results, Examples 1-4 cause no crystal precipitation. In other words, mixing of ondansetron with dexamethasone, followed by pH adjustment using an acid such as citric acid provides a stable composition for preventing nausea or vomiting. On the contrary, the composition adjusted to pH 2.5 causes drug crystal precipitation.

COMPARATIVE EXAMPLE 3

Preparation of Mixture of Ramosetron Hydrochloride with Dexamethasone Disodium Phosphate Comparative Example 3 is provided by simple mixing of 2 mL of the conventional injection composition of ramosetron hydrochloride with 2 mL of the conventional aqueous composition of dexamethasone disodium phosphate. Each composition has an effect of preventing nausea or vomiting.

1) Conventional Injection Composition of Ramosetron Hydrochloride
  Ramosetron hydrochloride: 0.15 mg/mL
  Isotonic agent: 9.0 mg/mL
  Lactic acid: 1.13 mg/mL
  pH modifier: adequate amount
  pH of aqueous solution: 4.5

2) Conventional Injection Composition of Dexamethasone Disodium Phosphate
  dexamethasone disodium phosphate: 5 mg/mL
  pH of aqueous composition: 7.7

White crystal precipitation occurs right after the mixing, and the mixed aqueous solution has a pH of 6.7. It can be seen from the above result that simple mixing of the two injection compositions cannot provide a stable composition.

EXAMPLES 5-8 AND COMPARATIVE EXAMPLE 4

Preparation of Mixture of Ramosetron Hydrochloride with Dexamethasone Disodium Phosphate Examples 5-8 and Comparative Example 4 are provided by using the compositions and amounts as shown in the following Table 2. More particularly, ramosetron hydrochloride dehydrate is added to and dissolved in 40 mL of 0.9% saline for injection. Then, dexamethasone disodium phosphate is added thereto and the mixture is agitated. When white crystal precipitation occurs, citric acid monohydrate is added in an adequate amount to form a clear solution. The aqueous solution is adjusted to a pH range of 3.0-4.5 by adding sodium citrate. Then, distilled water for injection is added to the aqueous solution, until the total volume of the aqueous solution becomes 25 or 50 mL. The mixed solution is sterilized with a sterilization filter having a pore size of 0.22 μm, and an aliquot of 5 mL of each sample is put into a 10 mL injection vial, followed by sealing. In this manner, Examples 5-8 are provided. Comparative Example 4 is provided by adding 0.1N HCl instead of citric acid to adjust the pH to 2.5. After the sample preparation, each sample is observed for crystal precipitation.

TABLE 2

| Example | Ramosetron hydrochloride (mg) | Dexamethasone disodium phosphate (mg) | Volume of Aqueous Solution (mL) | Precipitation pH | |
|---|---|---|---|---|---|
| Example 5 | 3 | 100 | 50 | 4.0 | Clear |
| Example 6 | 3 | 100 | 25 | 4.0 | Clear |
| Example 7 | 5 | 150 | 50 | 4.0 | Clear |
| Example 8 | 6 | 200 | 50 | 4.0 | Clear |
| Comparative Example 4 | 3 | 100 | 50 | 2.5 | Precipitation |

As can be seen from the above results, Examples 5-8 cause no crystal precipitation. In other words, mixing of ramosetron with dexamethasone, followed by pH adjustment using an acid such as citric acid provides a stable composition for preventing nausea or vomiting. On the contrary, the composition adjusted to pH 2.5 causes drug crystal precipitation.

The present application contains subject matter related to Korean Patent Application No. 10-2010-0135761, filed in the Korean Intellectual Property Office on Dec. 27, 2010, the entire contents of which is incorporated herein by reference.

Those skilled in the art will appreciate that the conceptions and specific embodiments disclosed in the foregoing description may be readily utilized as a basis for modifying or designing other embodiments for carrying out the same purposes of the present disclosure. Those skilled in the art will also appreciate that such equivalent embodiments do not depart from the spirit and scope of the disclosure as set forth in the appended claims.

We claim:

1. A method for preparing a composition, comprising:
   mixing a 5-$HT_3$ receptor antagonist with a corticosteroid; and
   adjusting pH of the mixture obtained from said mixing to 3.0 or higher but less than 6.0,
   wherein the 5-$HT_3$ receptor antagonist comprises at least one selected from ondansetron, ramosetron, derivatives thereof and pharmaceutically acceptable salts thereof,
   wherein the corticosteroid comprises at least one selected from dexamethasone, derivatives thereof and pharmaceutically acceptable salts thereof,
   wherein the concentration of the 5-$HT_3$ receptor antagonist is 0.0-10 mg/ml, and
   wherein the concentration of the corticosteroid is 1-4 mg/ml.

2. The method according to claim 1, wherein said adjusting pH is carried out by using a pH modifier or a buffering agent.

3. The method according to claim 2, wherein the pH modifier comprises at least one selected from the group consisting of organic acids, hydrochloric acid, phosphoric acid, carbonic acid and cyanic acid; and the buffering agent comprises at least one selected from the group consisting of organic acid buffers, phosphate buffers and carbonate buffers.

4. The method according to claim 1, wherein the composition is a liquid composition.

5. A composition comprising a 5-$HT_3$ receptor antagonist and a corticosteroid, and having a pH adjusted to 3.0 or higher but less than 6.0,
   wherein the 5-$HT_3$ receptor antagonist comprises at least one selected from ondansetron, ramosetron, derivatives thereof and pharmaceutically acceptable salts thereof,
   wherein the corticosteroid comprises at least one selected from dexamethasone, derivatives thereof and pharmaceutically acceptable salts thereof,
   wherein the concentration of the 5-$HT_3$ receptor antagonist is 0.01-10 mg/ml, and
   wherein the concentration of the corticosteroid is 1-4 mg/ml.

6. The composition according to claim 5, wherein the composition further comprises a pH modifier or a buffering agent.

7. The composition according to claim 6, wherein the pH modifier comprises at least one selected from the group consisting of organic acids, hydrochloric acid, phosphoric acid, carbonic acid and cyanic acid.

8. The composition according to claim 6, wherein the buffering agent comprises at least one selected from the group consisting of organic acid buffers, phosphate buffers and carbonate buffers.

9. The composition according to claim 5, wherein the composition is a liquid composition.

* * * * *